(12) United States Patent
Ballou, Jr. et al.

(10) Patent No.: US 8,733,935 B2
(45) Date of Patent: May 27, 2014

(54) METHOD AND SYSTEM FOR PERFORMING REMOTE TREATMENT AND MONITORING

(75) Inventors: Bernard L. Ballou, Jr., Raleigh, NC (US); Jurgen Klaus Vollrath, Indian Trail, NC (US); Kelly C. Sparks, Raleigh, NC (US); Joshua Richard Brown, Hickory, NC (US); Mark Packer, Eugene, OR (US); Charles Eric Hunter, Boone, NC (US); Troy Elliott, Raleigh, NC (US); John H. Hebrank, Durham, NC (US)

(73) Assignee: Corinthian Ophthalmic, Inc., Raleigh, NC (US)

( * ) Notice: Subject to any disclaimer, the term of this patent is extended or adjusted under 35 U.S.C. 154(b) by 138 days.

(21) Appl. No.: 13/184,468

(22) Filed: Jul. 15, 2011

(65) Prior Publication Data
US 2012/0062840 A1   Mar. 15, 2012

Related U.S. Application Data

(60) Provisional application No. 61/400,864, filed on Jul. 15, 2010, provisional application No. 61/401,850, filed on Aug. 20, 2010, provisional application No. 61/401,920, filed on Aug. 20, 2010, provisional application No. 61/401,918, filed on Aug. 20, 2010, provisional application No. 61/401,848, filed on Aug. 20, 2010, provisional application No. 61/401,849, filed on Aug. 20, 2010, provisional application No. 61/462,576, filed on Feb. 4, 2011, provisional application No. 61/462,791, filed on Feb. 5, 2011, provisional application No. 61/463,280, filed on Feb. 15, 2011, provisional application No. 61/516,462, filed on Apr. 4, 2011, provisional application No. 61/516,496, filed on Apr. 4, 2011, provisional application No. 61/516,495, filed on Apr. 4, 2011, provisional application No. 61/516,694, filed on Apr. 6, 2011.

(51) Int. Cl.
*A61B 3/14* (2006.01)
*A61F 7/00* (2006.01)
*A61B 3/113* (2006.01)
*A61B 3/117* (2006.01)
*A61F 9/00* (2006.01)

(52) U.S. Cl.
CPC ............. *A61B 3/113* (2013.01); *A61B 3/117* (2013.01); *A61F 9/0026* (2013.01)
USPC ................... 351/210; 604/294; 604/298

(58) Field of Classification Search
CPC ........ A61B 3/113; A61B 3/117; A61F 9/0026
USPC ........ 351/200, 205, 206, 210, 246; 606/4, 11; 604/294–300
See application file for complete search history.

(56) References Cited

U.S. PATENT DOCUMENTS

| 1,482,747 A | 2/1924 | Howe |
| 1,988,637 A | 1/1935 | Tinkham |

(Continued)

FOREIGN PATENT DOCUMENTS

| DE | 196 16 300 A1 | 10/1997 |
| DE | 19616300 A1 | 10/1997 |

(Continued)

OTHER PUBLICATIONS

"Alcon®: Sharing One Vision," 2009 Annual Report, 46 pages (2009).

(Continued)

*Primary Examiner* — Huy K Mai
(74) *Attorney, Agent, or Firm* — Polsinelli PC

(57) ABSTRACT

The disclosure relates to medical databases, remote monitoring, diagnosis and treatment systems and methods. In one particular embodiment, a system for remote monitoring, diagnosis, or treatment of eye conditions, disorders and diseases is provided. This method generally includes administering a stream of droplets to the eye of a subject from an ejector device, and storing data related to the administration in a memory of the ejector device. The data may then be monitored and analyzed.

21 Claims, 6 Drawing Sheets

(56) References Cited

U.S. PATENT DOCUMENTS

| | | |
|---|---|---|
| 2,189,643 A | 2/1940 | Ward |
| 2,200,008 A | 5/1940 | Nowak |
| 2,249,608 A | 7/1941 | Greene |
| 2,322,808 A | 6/1943 | Hothersall |
| 2,552,857 A | 5/1951 | Knapp |
| 2,595,317 A | 5/1952 | White |
| 2,987,439 A | 6/1961 | Wittlinger |
| 3,170,462 A | 2/1965 | Hall |
| 3,187,757 A | 6/1965 | Jones et al. |
| 3,237,809 A | 3/1966 | Daragan et al. |
| 3,310,830 A | 3/1967 | Gattone |
| 3,314,426 A | 4/1967 | Caroll |
| 3,439,674 A | 4/1969 | Lelicoff |
| 3,602,399 A | 8/1971 | Litman et al. |
| 3,658,257 A | 4/1972 | Rood |
| 3,709,235 A | 1/1973 | Washburn et al. |
| 3,779,245 A | 12/1973 | Windsor |
| 3,780,950 A | 12/1973 | Brennan |
| 3,795,351 A | 3/1974 | Lehmann |
| 3,812,854 A | 5/1974 | Michaels et al. |
| 3,826,258 A | 7/1974 | Abraham |
| 3,845,764 A | 11/1974 | Windsor |
| 3,901,443 A | 8/1975 | Mitsui et al. |
| 3,906,949 A | 9/1975 | Holland |
| 3,913,575 A | 10/1975 | Windsor |
| 3,934,585 A | 1/1976 | Maurice |
| 4,002,168 A | 1/1977 | Petterson |
| 4,012,798 A | 3/1977 | Liautaud |
| 4,052,985 A | 10/1977 | Coleman et al. |
| 4,067,499 A | 1/1978 | Cohen |
| 4,098,431 A | 7/1978 | Palmer et al. |
| D249,709 S | 9/1978 | Trovinger |
| 4,119,096 A | 10/1978 | Drews |
| 4,122,556 A | 10/1978 | Poler |
| 4,131,115 A | 12/1978 | Peng |
| 4,173,226 A | 11/1979 | Shell |
| 4,175,704 A | 11/1979 | Cohen |
| 4,175,706 A | 11/1979 | Gerstmann |
| 4,264,837 A | 4/1981 | Gaboriaud |
| 4,296,071 A | 10/1981 | Weiss et al. |
| 4,319,155 A | 3/1982 | Nakai et al. |
| 4,323,530 A | 4/1982 | Voss et al. |
| 4,338,936 A | 7/1982 | Nelson |
| 4,356,528 A | 10/1982 | Coffee |
| 4,381,533 A | 4/1983 | Coffee |
| 4,388,343 A | 6/1983 | Voss et al. |
| 4,390,542 A | 6/1983 | Schachar |
| 4,398,909 A | 8/1983 | Portnoff |
| 4,465,234 A | 8/1984 | Maehara et al. |
| 4,471,890 A | 9/1984 | Dougherty |
| 4,476,515 A | 10/1984 | Coffee |
| 4,479,609 A | 10/1984 | Maeda et al. |
| 4,493,119 A | 1/1985 | Baumann |
| 4,543,096 A | 9/1985 | Keene |
| 4,544,570 A | 10/1985 | Plunkett et al. |
| 4,564,016 A | 1/1986 | Maurice et al. |
| 4,580,721 A | 4/1986 | Coffee et al. |
| 4,605,167 A | 8/1986 | Maehara |
| 4,605,398 A | 8/1986 | Herrick |
| 4,627,845 A | 12/1986 | DeMotte |
| 4,641,384 A | 2/1987 | Landsberger et al. |
| 4,642,581 A | 2/1987 | Erickson |
| 4,658,290 A | 4/1987 | McKenna et al. |
| 4,659,014 A | 4/1987 | Soth et al. |
| 4,679,551 A | 7/1987 | Anthony |
| 4,685,906 A | 8/1987 | Murphy |
| 4,701,167 A | 10/1987 | Chekan |
| 4,702,418 A | 10/1987 | Carter et al. |
| 4,706,848 A | 11/1987 | D'Andrade |
| 4,740,206 A | 4/1988 | Allander |
| 4,742,713 A | 5/1988 | Abe et al. |
| 4,750,650 A | 6/1988 | Ling |
| 4,750,902 A | 6/1988 | Wuchinich et al. |
| 4,758,237 A | 7/1988 | Sacks |
| 4,758,727 A | 7/1988 | Tomei et al. |
| 4,759,755 A | 7/1988 | Hein et al. |
| 4,779,768 A | 10/1988 | St. Amand |
| 4,784,652 A | 11/1988 | Wikström |
| 4,790,479 A | 12/1988 | Matsumoto et al. |
| 4,792,334 A | 12/1988 | Py |
| 4,793,339 A | 12/1988 | Matsumoto et al. |
| 4,796,807 A | 1/1989 | Bendig et al. |
| 4,798,599 A | 1/1989 | Thomas |
| 4,809,914 A | 3/1989 | Goncalves |
| 4,815,661 A | 3/1989 | Anthony |
| 4,826,025 A | 5/1989 | Abiko et al. |
| 4,850,534 A | 7/1989 | Takahashi et al. |
| 4,863,073 A | 9/1989 | Burt et al. |
| 4,863,443 A | 9/1989 | Hornung |
| 4,863,457 A | 9/1989 | Lee |
| 4,871,091 A | 10/1989 | Preziosi |
| 4,877,989 A | 10/1989 | Drews et al. |
| 4,880,146 A | 11/1989 | Hudgins |
| 4,881,283 A | 11/1989 | Liautaud |
| 4,886,189 A | 12/1989 | Vanderjagt |
| 4,896,832 A | 1/1990 | Howlett |
| 4,908,024 A | 3/1990 | Py |
| 4,912,357 A | 3/1990 | Drews et al. |
| 4,917,274 A | 4/1990 | Asa et al. |
| 4,927,062 A | 5/1990 | Walsh |
| 4,927,115 A | 5/1990 | Bahroos et al. |
| 4,946,452 A | 8/1990 | Py |
| 4,952,212 A | 8/1990 | Booth et al. |
| 4,961,885 A | 10/1990 | Avrahami et al. |
| 4,969,869 A | 11/1990 | Burgin et al. |
| 4,981,479 A | 1/1991 | Py |
| 4,996,502 A | 2/1991 | Endo |
| 5,007,905 A | 4/1991 | Bauer |
| 5,019,037 A | 5/1991 | Wang et al. |
| 5,029,579 A | 7/1991 | Trammell |
| 5,030,214 A | 7/1991 | Spector |
| 5,032,111 A | 7/1991 | Morris et al. |
| 5,037,012 A | 8/1991 | Langford |
| 5,040,706 A | 8/1991 | Davis et al. |
| 5,047,009 A | 9/1991 | Morris et al. |
| 5,048,727 A | 9/1991 | Vlasich |
| 5,053,000 A | 10/1991 | Booth et al. |
| 5,054,477 A | 10/1991 | Terada et al. |
| 5,064,420 A | 11/1991 | Clarke et al. |
| 5,066,276 A | 11/1991 | Wang |
| 5,069,204 A | 12/1991 | Smith et al. |
| 5,069,675 A | 12/1991 | Menchel et al. |
| 5,085,651 A | 2/1992 | Py |
| 5,098,375 A | 3/1992 | Baier |
| 5,133,702 A | 7/1992 | Py |
| 5,134,993 A | 8/1992 | van der Linden et al. |
| 5,139,496 A | 8/1992 | Hed |
| 5,145,113 A | 9/1992 | Burwell et al. |
| 5,152,435 A | 10/1992 | Stand et al. |
| 5,152,456 A | 10/1992 | Ross et al. |
| 5,163,929 A | 11/1992 | Py |
| 5,164,740 A | 11/1992 | Ivri |
| 5,170,782 A | 12/1992 | Kocinski |
| 5,171,306 A | 12/1992 | Vo |
| 5,176,856 A | 1/1993 | Takahashi et al. |
| 5,193,745 A | 3/1993 | Holm |
| 5,201,726 A | 4/1993 | Kirkham |
| 5,203,506 A | 4/1993 | Gross et al. |
| 5,226,538 A | 7/1993 | Roselle |
| 5,252,318 A | 10/1993 | Joshi et al. |
| 5,259,385 A | 11/1993 | Miller et al. |
| 5,261,601 A | 11/1993 | Ross et al. |
| 5,265,288 A | 11/1993 | Allison |
| 5,267,986 A | 12/1993 | Py |
| 5,276,867 A | 1/1994 | Kenley et al. |
| 5,299,739 A | 4/1994 | Takahashi et al. |
| 5,316,159 A | 5/1994 | Douglas et al. |
| 5,318,014 A | 6/1994 | Carter |
| 5,320,845 A | 6/1994 | Py |
| 5,354,032 A | 10/1994 | Sims et al. |
| 5,364,405 A | 11/1994 | Zaleski |
| 5,368,582 A | 11/1994 | Bertera |
| 5,401,259 A | 3/1995 | Py |
| 5,405,614 A | 4/1995 | D'Angelo et al. |

(56) References Cited

U.S. PATENT DOCUMENTS

| | | |
|---|---|---|
| 5,431,663 A | 7/1995 | Carter |
| 5,435,282 A | 7/1995 | Haber et al. |
| 5,435,465 A | 7/1995 | El-Amin |
| 5,462,586 A | 10/1995 | Sugiyama et al. |
| 5,485,828 A | 1/1996 | Hauser |
| 5,496,411 A | 3/1996 | Candy |
| 5,499,751 A | 3/1996 | Meyer |
| D368,774 S | 4/1996 | Py |
| 5,515,841 A | 5/1996 | Robertson et al. |
| 5,518,179 A | 5/1996 | Humberstone et al. |
| 5,529,055 A | 6/1996 | Gueret |
| D374,719 S | 10/1996 | Py |
| 5,564,016 A | 10/1996 | Korenshtein |
| 5,584,823 A | 12/1996 | Valberg |
| 5,586,550 A | 12/1996 | Ivri et al. |
| 5,588,564 A | 12/1996 | Hutson et al. |
| 5,607,410 A | 3/1997 | Branch |
| 5,613,957 A | 3/1997 | Py |
| 5,614,545 A | 3/1997 | Martin et al. |
| 5,630,793 A | 5/1997 | Rowe |
| 5,657,926 A | 8/1997 | Toda |
| 5,665,079 A | 9/1997 | Stahl |
| 5,685,869 A | 11/1997 | Py |
| 5,687,874 A | 11/1997 | Omori et al. |
| 5,707,636 A | 1/1998 | Rodriguez et al. |
| 5,724,021 A | 3/1998 | Perrone |
| 5,730,723 A | 3/1998 | Castellano et al. |
| 5,735,811 A | 4/1998 | Brisken |
| 5,740,947 A | 4/1998 | Flaig et al. |
| 5,746,728 A | 5/1998 | Py |
| 5,758,637 A | 6/1998 | Ivri et al. |
| 5,803,106 A | 9/1998 | Cohen et al. |
| 5,807,357 A | 9/1998 | Kang |
| 5,823,428 A | 10/1998 | Humberstone et al. |
| 5,838,350 A | 11/1998 | Newcombe et al. |
| 5,843,109 A | 12/1998 | Mehta et al. |
| 5,855,322 A | 1/1999 | Py |
| 5,881,956 A | 3/1999 | Cohen et al. |
| 5,893,515 A | 4/1999 | Hahn et al. |
| 5,894,841 A | 4/1999 | Voges |
| 5,938,117 A | 8/1999 | Ivri |
| D413,668 S | 9/1999 | Mannberg et al. |
| 5,957,943 A | 9/1999 | Vaitekunas |
| 5,970,974 A | 10/1999 | Van Der Linden et al. |
| 5,996,903 A | 12/1999 | Asai et al. |
| 5,997,518 A | 12/1999 | Laibovitz et al. |
| 6,008,468 A | 12/1999 | Tanaka et al. |
| 6,027,450 A | 2/2000 | Brown |
| 6,039,565 A | 3/2000 | Chou et al. |
| 6,062,212 A | 5/2000 | Davison et al. |
| 6,083,922 A | 7/2000 | Montgomery |
| 6,085,740 A | 7/2000 | Ivri et al. |
| 6,135,427 A | 10/2000 | Tsai |
| 6,152,383 A | 11/2000 | Chen |
| 6,159,188 A | 12/2000 | Laibovitz et al. |
| 6,193,683 B1 | 2/2001 | Ludin et al. |
| 6,203,759 B1 | 3/2001 | Pelc et al. |
| 6,216,966 B1 | 4/2001 | Prendergast et al. |
| 6,221,038 B1 | 4/2001 | Brisken |
| 6,228,046 B1 | 5/2001 | Brisken |
| 6,235,024 B1 | 5/2001 | Tu |
| 6,254,579 B1 | 7/2001 | Cogger et al. |
| 6,254,587 B1 | 7/2001 | Christ et al. |
| 6,263,872 B1 | 7/2001 | Schuster et al. |
| 6,273,342 B1 | 8/2001 | Terada et al. |
| 6,296,626 B1 | 10/2001 | Stein |
| 6,318,361 B1 | 11/2001 | Sosiak |
| 6,336,917 B1 | 1/2002 | Berke |
| 6,341,732 B1 | 1/2002 | Martin et al. |
| 6,357,442 B1 | 3/2002 | Casper et al. |
| 6,357,671 B1 | 3/2002 | Cewers |
| 6,367,685 B1 | 4/2002 | Jiang et al. |
| 6,394,363 B1 | 5/2002 | Arnott et al. |
| 6,398,737 B2 | 6/2002 | Moore et al. |
| 6,398,766 B1 | 6/2002 | Branch |
| 6,422,431 B2 | 7/2002 | Pelc et al. |
| 6,423,040 B1 | 7/2002 | Benktzon et al. |
| 6,425,888 B1 | 7/2002 | Embleton et al. |
| 6,427,682 B1 | 8/2002 | Klimowicz et al. |
| 6,442,423 B1 | 8/2002 | Domb et al. |
| 6,443,146 B1 | 9/2002 | Voges |
| 6,467,476 B1 | 10/2002 | Ivri et al. |
| 6,524,287 B1 | 2/2003 | Cogger |
| 6,526,976 B1 | 3/2003 | Baran |
| 6,530,370 B1 | 3/2003 | Heinonen |
| 6,540,153 B1 | 4/2003 | Ivri |
| 6,540,154 B1 | 4/2003 | Ivri et al. |
| 6,543,443 B1 | 4/2003 | Klimowicz et al. |
| 6,546,927 B2 | 4/2003 | Litherland et al. |
| 6,550,472 B2 | 4/2003 | Litherland et al. |
| 6,554,201 B2 | 4/2003 | Klimowicz et al. |
| 6,554,801 B1 | 4/2003 | Steward et al. |
| 6,569,131 B1 | 5/2003 | Michael et al. |
| 6,569,387 B1 | 5/2003 | Furner et al. |
| 6,601,581 B1 | 8/2003 | Babaev |
| 6,610,033 B1 | 8/2003 | Melanson et al. |
| 6,612,302 B1 | 9/2003 | Rand |
| 6,615,824 B2 | 9/2003 | Power |
| 6,619,562 B2 | 9/2003 | Hamaguchi et al. |
| 6,622,720 B2 | 9/2003 | Hadimioglu |
| 6,629,646 B1 | 10/2003 | Ivri |
| 6,640,804 B2 | 11/2003 | Ivri et al. |
| 6,650,935 B1 | 11/2003 | Watmough |
| 6,651,650 B1 | 11/2003 | Yamamoto et al. |
| 6,659,364 B1 | 12/2003 | Humberstone et al. |
| 6,669,961 B2 | 12/2003 | Kim et al. |
| 6,676,034 B2 | 1/2004 | Tanaka et al. |
| 6,679,436 B1 | 1/2004 | Onishi et al. |
| 6,684,681 B1 | 2/2004 | Zombo |
| 6,684,879 B1 | 2/2004 | Coffee et al. |
| 6,719,770 B2 | 4/2004 | Laufer et al. |
| 6,732,944 B2 | 5/2004 | Litherland et al. |
| 6,736,904 B2 | 5/2004 | Poniatowski et al. |
| 6,740,107 B2 | 5/2004 | Loeb et al. |
| 6,748,944 B1 | 6/2004 | Della Vecchia et al. |
| 6,761,286 B2 | 7/2004 | Py et al. |
| 6,789,741 B2 | 9/2004 | Varanasi et al. |
| 6,814,071 B2 | 11/2004 | Klimowicz et al. |
| 6,851,626 B2 | 2/2005 | Patel et al. |
| 6,854,662 B2 | 2/2005 | Chen |
| 6,863,224 B2 | 3/2005 | Terada et al. |
| 6,877,642 B1 | 4/2005 | Maddox et al. |
| 6,885,818 B2 | 4/2005 | Goldstein |
| 6,901,926 B2 | 6/2005 | Yamamoto et al. |
| 6,913,205 B2 | 7/2005 | Cornet et al. |
| 6,921,020 B2 | 7/2005 | Ivri |
| 6,926,208 B2 | 8/2005 | Ivri |
| 6,946,117 B1 | 9/2005 | Schutt et al. |
| 6,964,647 B1 | 11/2005 | Babaev |
| 6,969,165 B2 | 11/2005 | Olsen |
| 6,974,450 B2 | 12/2005 | Weber et al. |
| 6,976,279 B1 | 12/2005 | Berke et al. |
| 6,976,969 B2 | 12/2005 | Messerly |
| 6,978,945 B2 | 12/2005 | Wong et al. |
| 7,017,573 B1 | 3/2006 | Rasor et al. |
| 7,032,590 B2 | 4/2006 | Loeffler et al. |
| 7,040,549 B2 | 5/2006 | Ivri et al. |
| 7,066,398 B2 | 6/2006 | Borland et al. |
| 7,081,757 B2 | 7/2006 | Unsworth et al. |
| 7,083,112 B2 | 8/2006 | Ivri |
| 7,104,463 B2 | 9/2006 | Litherland et al. |
| 7,108,197 B2 | 9/2006 | Ivri |
| 7,121,275 B2 | 10/2006 | Noolandi et al. |
| D533,658 S | 12/2006 | Collins, Jr. et al. |
| 7,153,315 B2 | 12/2006 | Miller |
| 7,161,269 B2 | 1/2007 | Kayama et al. |
| 7,168,633 B2 | 1/2007 | Wang et al. |
| D537,160 S | 2/2007 | Lowell |
| 7,174,888 B2 | 2/2007 | Ivri et al. |
| 7,192,129 B2 | 3/2007 | Droege et al. |
| 7,201,732 B2 | 4/2007 | Anderson et al. |
| 7,204,820 B2 | 4/2007 | Akahoshi |
| 7,229,028 B2 | 6/2007 | Chen et al. |
| 7,234,460 B2 | 6/2007 | Greenleaf et al. |

(56) References Cited

U.S. PATENT DOCUMENTS

| | | |
|---|---|---|
| 7,314,187 B2 | 1/2008 | Hochrainer et al. |
| 7,316,067 B2 | 1/2008 | Blakey |
| 7,331,339 B2 | 2/2008 | Smith et al. |
| 7,357,133 B2 | 4/2008 | Goodchild |
| 7,472,701 B2 | 1/2009 | Pfichner et al. |
| D597,206 S | 7/2009 | Collins, Jr. et al. |
| 7,574,787 B2 | 8/2009 | Xu et al. |
| 7,678,089 B2 | 3/2010 | Py et al. |
| 7,712,466 B2 | 5/2010 | Addington et al. |
| 7,819,115 B2 | 10/2010 | Sexton et al. |
| 7,883,031 B2 | 2/2011 | Collins, Jr. et al. |
| 8,012,136 B2 | 9/2011 | Collins, Jr. et al. |
| 2001/0025190 A1 | 9/2001 | Weber et al. |
| 2001/0049608 A1 | 12/2001 | Hochman |
| 2001/0056258 A1 | 12/2001 | Evans |
| 2002/0016576 A1 | 2/2002 | Lee |
| 2002/0039502 A1 | 4/2002 | Matsumoto et al. |
| 2002/0043262 A1 | 4/2002 | Langford et al. |
| 2002/0073989 A1 | 6/2002 | Hadimioglu |
| 2002/0074362 A1 | 6/2002 | Py et al. |
| 2002/0107492 A1 | 8/2002 | Brach et al. |
| 2002/0121285 A1 | 9/2002 | Poniatowski et al. |
| 2002/0124843 A1 | 9/2002 | Skiba et al. |
| 2002/0161344 A1 | 10/2002 | Peclat et al. |
| 2003/0032930 A1 | 2/2003 | Branch |
| 2003/0078551 A1 | 4/2003 | Hochrainer et al. |
| 2003/0114901 A1 | 6/2003 | Loeb et al. |
| 2003/0144594 A1 | 7/2003 | Gellman |
| 2003/0185892 A1 | 10/2003 | Bell et al. |
| 2003/0192532 A1 | 10/2003 | Hopkins |
| 2004/0010239 A1 | 1/2004 | Hochrainer et al. |
| 2004/0039355 A1* | 2/2004 | Gonzalez et al. ............ 604/298 |
| 2004/0045547 A1 | 3/2004 | Yamamoto et al. |
| 2004/0050953 A1 | 3/2004 | Terada et al. |
| 2004/0082884 A1 | 4/2004 | Pal et al. |
| 2004/0164099 A1 | 8/2004 | Diestelhorst et al. |
| 2004/0176757 A1 | 9/2004 | Sinelnikov et al. |
| 2004/0186384 A1 | 9/2004 | Babaev |
| 2004/0204674 A1 | 10/2004 | Anderson et al. |
| 2004/0256487 A1 | 12/2004 | Collins, Jr. et al. |
| 2005/0001981 A1 | 1/2005 | Anderson et al. |
| 2005/0029307 A1 | 2/2005 | Py et al. |
| 2005/0077315 A1 | 4/2005 | Pavlu et al. |
| 2005/0077392 A1 | 4/2005 | Geser et al. |
| 2005/0089545 A1 | 4/2005 | Kuwano et al. |
| 2005/0195598 A1 | 9/2005 | Dancs et al. |
| 2005/0199236 A1 | 9/2005 | Fink et al. |
| 2005/0240162 A1 | 10/2005 | Chen et al. |
| 2005/0244339 A1 | 11/2005 | Jauernig et al. |
| 2005/0261641 A1 | 11/2005 | Warchol et al. |
| 2005/0263608 A1 | 12/2005 | Ivri |
| 2005/0275310 A1 | 12/2005 | Ripoll |
| 2005/0279350 A1 | 12/2005 | Rasor et al. |
| 2006/0024374 A1 | 2/2006 | Gasco et al. |
| 2006/0057216 A1 | 3/2006 | Salamone et al. |
| 2006/0174869 A1 | 8/2006 | Gumaste et al. |
| 2006/0196518 A1 | 9/2006 | Hon |
| 2006/0201501 A1 | 9/2006 | Morrison et al. |
| 2006/0209129 A1 | 9/2006 | Onozawa |
| 2006/0213503 A1 | 9/2006 | Borgschulte et al. |
| 2006/0258993 A1 | 11/2006 | Hochrainer et al. |
| 2007/0023547 A1 | 2/2007 | Borland et al. |
| 2007/0044792 A1 | 3/2007 | Ivri |
| 2007/0113841 A1 | 5/2007 | Fuchs |
| 2007/0119968 A1 | 5/2007 | Collins, Jr. et al. |
| 2007/0119969 A1 | 5/2007 | Collins, Jr. et al. |
| 2007/0211212 A1* | 9/2007 | Bennwik ............ 351/221 |
| 2008/0017189 A1 | 1/2008 | Ruckdeschel et al. |
| 2008/0097359 A1 | 4/2008 | Hochrainer et al. |
| 2008/0142624 A1 | 6/2008 | Ivri et al. |
| 2008/0164339 A1 | 7/2008 | Duru |
| 2008/0233053 A1 | 9/2008 | Gross et al. |
| 2008/0299049 A1 | 12/2008 | Stangl |
| 2008/0303850 A1* | 12/2008 | Shin et al. ............ 347/9 |
| 2008/0308096 A1 | 12/2008 | Borgschulte et al. |
| 2009/0025713 A1 | 1/2009 | Keller et al. |
| 2009/0114742 A1 | 5/2009 | Collins, Jr. |
| 2009/0149829 A1 | 6/2009 | Collins, Jr. |
| 2009/0192443 A1 | 7/2009 | Collins, Jr. et al. |
| 2009/0212133 A1 | 8/2009 | Collins, Jr. et al. |
| 2010/0044460 A1 | 2/2010 | Sauzade |
| 2010/0211408 A1* | 8/2010 | Park et al. ............ 705/3 |
| 2010/0222752 A1 | 9/2010 | Collins, Jr. |
| 2010/0283601 A1 | 11/2010 | Tai et al. |
| 2012/0143152 A1* | 6/2012 | Hunter et al. ............ 604/298 |

FOREIGN PATENT DOCUMENTS

| | | |
|---|---|---|
| DE | 199 34 582 A1 | 1/2001 |
| EP | 0 011 269 A1 | 5/1980 |
| EP | 0 150 571 A1 | 8/1985 |
| EP | 0 224 352 A1 | 6/1987 |
| EP | 0 389 665 A1 | 10/1990 |
| EP | 0 590 165 A1 | 4/1994 |
| EP | 0 823 246 A2 | 2/1996 |
| EP | 0 933 138 A2 | 8/1999 |
| EP | 1493410 A2 | 1/2005 |
| EP | EP 1 493 410 A2 | 1/2005 |
| FR | 1 271 341 | 7/1961 |
| GB | 558866 | 7/1942 |
| GB | 1 569 707 | 7/1980 |
| TW | I293898 | 7/1994 |
| WO | WO 85/00761 A1 | 2/1985 |
| WO | WO 91/12687 A1 | 8/1991 |
| WO | WO 91/14468 A1 | 10/1991 |
| WO | WO 94/13305 A1 | 6/1994 |
| WO | WO 94/23788 A1 | 10/1994 |
| WO | WO 97/05960 A1 | 2/1997 |
| WO | WO 97/12687 A1 | 4/1997 |
| WO | WO 98/19383 A1 | 5/1998 |
| WO | WO 99/17888 A1 | 4/1999 |
| WO | WO 00/18455 A1 | 4/2000 |
| WO | WO 00/66277 A1 | 11/2000 |
| WO | WO 01/03645 A2 | 1/2001 |
| WO | WO 01/19437 A2 | 3/2001 |
| WO | WO 01/58236 A2 | 8/2001 |
| WO | WO 01/85245 A1 | 11/2001 |
| WO | WO 02/28545 A1 | 4/2002 |
| WO | WO 02/055131 A2 | 7/2002 |
| WO | 02/062488 A1 | 8/2002 |
| WO | WO 02/062488 A1 | 8/2002 |
| WO | WO 02/072169 A2 | 9/2002 |
| WO | WO 03/002045 A1 | 1/2003 |
| WO | WO 03/002265 A1 | 1/2003 |
| WO | WO 03/026556 A2 | 4/2003 |
| WO | WO 03/097139 A1 | 11/2003 |
| WO | 2004/028420 A1 | 4/2004 |
| WO | WO 2004/028420 A1 | 4/2004 |
| WO | WO 2004/050065 A1 | 6/2004 |
| WO | WO 2004/103478 A1 | 12/2004 |
| WO | WO 2004/105864 A1 | 12/2004 |
| WO | WO 2006/006963 A2 | 1/2006 |
| WO | WO 2006/082588 A2 | 8/2006 |
| WO | WO 2008/015394 A1 | 2/2008 |
| WO | 2009/148345 A2 | 12/2009 |
| WO | WO 2009/148345 A2 | 12/2009 |
| WO | WO 2012/009696 A2 | 1/2012 |
| WO | WO 2012/009706 A1 | 1/2012 |

OTHER PUBLICATIONS

Conover (Ed.), "View into the Future of Ophthalmology Treatments," *Healthcare Observer*, 1(8):2-37 (2009).

Dhand, "Nebulizers That Use a Vibrating Mesh or Plate with Multiple Apertures to Generate Aerosol," *Respir Care*, 47(12):1406-1418 (2002).

Donnelly et al., "Using ultrasonic atomization to produce and aerosol of micron-scale particles," *Review of Scientific Instruments*, 76:113301-1-113301-10 (2005).

Durnan et al., "Gold-Chlorine and Gold-Bromine Equilibria in Fused Salts," *The Journal of Physical Chemistry*, 68(4):847-850 (1964).

Galambos et al., "Drop ejection utilizing sideways actuation of a MEMS piston," *Sensors and Actuators A*, 141:182-191 (2008).

(56) References Cited

OTHER PUBLICATIONS

Hinds, *Aerosol Technology: Properties, Behavior, and Measurement of Airborene Particles*, pp. 42-71, 11-119, & 294-301 (1999).

Instruction Manual for Omron® Model NE-U03V MicroAir® Nebulizer, 20 pages (No date).

International Search Report mailed on Dec. 12, 2011, in International Application No. PCT/US2011/044291.

International Search Report mailed on Dec. 13, 2011, in International Application No. PCT/US2011/044286.

Product Description for Xalatan®: Iatanoprost ophthalmic solution, Pfizer Manufacturing, Belgium, NV, 8 pages (2009).

Quigley, "Improving Eye Drop Treatment for Glaucoma through Better Adherence," *Optometry and Vision Science*, 85(6):374-375 (2008).

Ranade et al., "Chapter seven: Intranasal and ocular drug delivery," *Drug Delivery Systems: Second Edition*, CLC Press, 39 pages (2004).

Rosen et al., "Printing High Viscosity Fluids Using Ultrasonic Droplet Generation," The George W. Woodruff School of Mechanical Engineering, Georgia Institute of Technology, pp. 239-253 (2008).

Shidhaye et al., "Novel drug delivery devices," *Pharma Times*, 38(7):24-27 (2006).

Tamilvanan et al., "The potential of lipid emulsion for ocular delivery of lipophilic drugs," *European Journal of Pharmaceutics and Biopharmaceutics*, 58:357-368 (2004).

Xia et al., "A potential application of a piezoelectric atomiser for ophthalmic drug delivery," *BOB*, 4(1):9-17 (2007).

Yee et al., "Trends in Glaucoma Treatment," EyeWorld Educational Symposium, San Francisco, 8 pages (2006).

Yuan et al., "MEMS-based piezoelectric array microjet," *Microelectronic Engineering*, 66:767-772 (2003).

\* cited by examiner

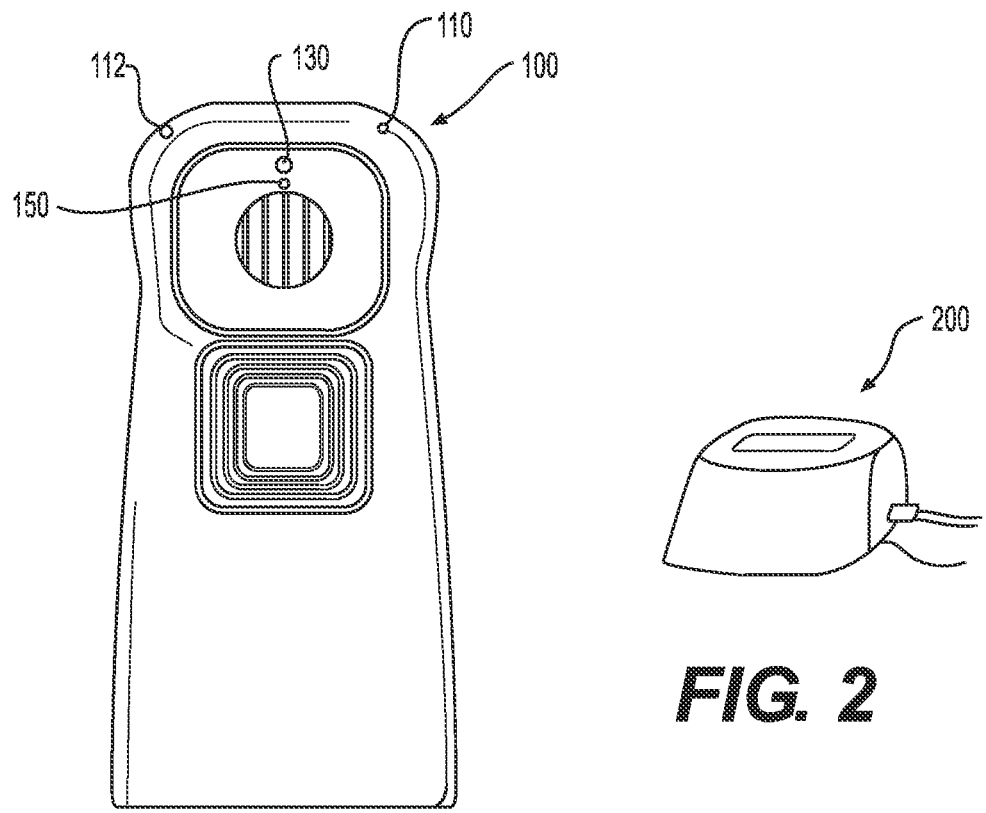
FIG. 1
FIG. 2
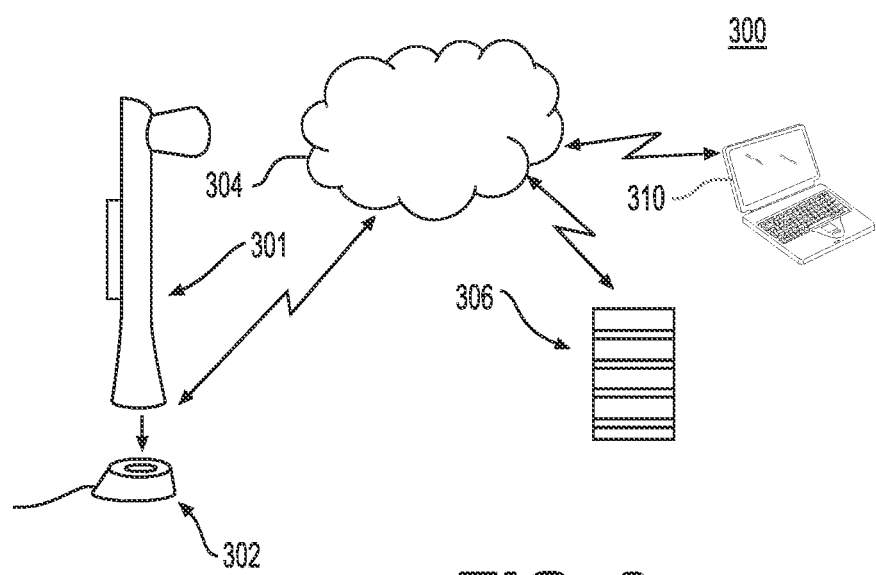
FIG. 3

METHOD AND SYSTEM FOR PERFORMING REMOTE TREATMENT AND MONITORING

RELATED APPLICATIONS

The present application claims the benefit of the filing date of U.S. Provisional Application No. 61/400,864, filed Jul. 15, 2010, U.S. Provisional Application No. 61/401,850, filed Aug. 20, 2010, U.S. Provisional Application No. 61/401,920 filed Aug. 20, 2010, U.S. Provisional Application No. 61/401,918 filed Aug. 20, 2010, U.S. Provisional Application No. 61/401,848 filed Aug. 20, 2010, U.S. Provisional Application No. 61/401,849 filed Aug. 20, 2010, U.S. Provisional Application No. 61/462,576 filed Feb. 4, 2011, U.S. Provisional Application No. 61/462,791 filed Feb. 5, 2011, U.S. Provisional Application No. 61/463,280 filed Feb. 15, 2011, U.S. Provisional Application No. 61/516,462, filed Apr. 4, 2011, U.S. Provisional Application No. 61/516,496 filed Apr. 4, 2011, U.S. Provisional Application No. 61/516,495 filed Apr. 4, 2011, and U.S. Provisional Application No. 61/516,694, filed Apr. 6, 2011, the entire contents of each of which is specifically hereby incorporated by reference for all purposes. The present application is also related to U.S. Provisional Application No. 61/396,531 filed May 28, 2010, the entire contents of which is specifically hereby incorporated by reference for all purposes.

FIELD OF THE INVENTION

The disclosure relates to medical systems and methods. In particular, it relates to medical database, remote monitoring, diagnosis and treatment systems and methods.

BACKGROUND OF THE INVENTION

The monitoring, diagnosis and treatment of various conditions, disorders and diseases, such as eye conditions, disorders, diseases, etc., typically involve the regular physical intervention by a medical professional, requiring the subject to make an appointment and visit the doctor's or practitioner's offices. On the part of the subject, this involves travel time to the doctor and back, a waiting period and typically a face-to-face discussion with a nurse practitioner or doctor's assistant, followed by a discussion and examination by a doctor. Insofar as the subject is issued with a prescription, he or she then has to proceed to a pharmacy, wait for the prescription to be filled and finally proceed home. Thus, the treatment and monitoring of subjects is a highly time-consuming exercise.

From the practitioner's or provider's perspective, the number of subjects he or she can see is limited by the face-to-face time with each subject to discuss the subject's condition, arrange slip lamps and other scanning devices, examine the subject, update the subject's records and record the tests conducted for compliance and insurance purposes.

Even when subjects are scheduled for follow-up examinations pursuant to the use of certain medications, the practitioner merely has the opportunity to determine whether there is a change in the subject's condition, but still remains unable to verify whether or not the subject has regularly taken the medication and has done so in the correct dose. This equally applies to veterinary doctors. Thus, notwithstanding the time-consuming nature of in-person examinations, the decisions that can be drawn from the analysis remain largely speculative and inconclusive.

Thus, comparisons to prior results of a particular subject, and comparisons to other subjects treated with the same drugs, can only act as an approximation due to the many unknowns. The inaccuracies in the results may be ascribed to both human error and the limitations of current dispensing devices. An additional problem is that subjects may forget to dose or double-dose or cross-dose with other medications. Even when subjects administer medication correctly (or have the medication correctly administered), current technology does not provide a satisfactory way of controlling the amount of medication that is dispensed, nor does it provide a way of ensuring that the medication that is dispensed actually reaches the eye and remains in the eye.

Current approaches fail to provide an accurate way of monitoring the administration of medication and dosages. The present disclosure addresses such shortcomings in addition to others.

SUMMARY OF THE INVENTION

In one aspect, according to the disclosure, there is provided a system for monitoring a subject, e.g., for compliance with a dosing regimen, for analysis of treatment, for diagnosis, etc., the system generally comprising at least one ejector device configured for administering a stream of droplets to the eye of a subject in need thereof, wherein the ejector device comprises a memory for storing subject-specific data and a communication interface for communicating said stored data. In certain embodiments, the system further comprises a docking station configured to interface with the ejector device and to communicate with said ejector device. In certain embodiments, the system comprises at least one database or server in communication with said ejector device. In some embodiments, the ejector device is in communication with said database or server via the docking station.

In another embodiment, methods are provided which generally include: (1) administering a stream of droplets to the eye of a subject in need thereof using an ejector device as described herein; and (2) storing data in a memory of the device, the data relating to, e.g., dosing regimen information, image information, etc. In certain embodiments, the method may further include (3) communicating the stored data from the ejector device, e.g., to a docking station, database or server, and/or user terminal. The communicated data may then be stored in memory in the docking station, the database or server, or in a memory on the user terminal. In yet other embodiments, the data communicated from the device (e.g., from the docking station, database or server, or via the user terminal) may be reviewed and analyzed. Based on such review and analysis, in one embodiment, the method may include adjusting dosages and medicaments as needed.

In another embodiment, the ejector device may include an image capturing device, and the method may include communicating image information (e.g., ocular image information). The method may include reviewing and analyzing the image information to diagnose the subject, e.g., by comparing image information to previous images obtained from the same subject or to images obtained from other subjects.

In another embodiment, approved providers may sign onto the system and through a user interface set parameters, with, for example, a look-up table, that the device will read to adjust dosage amounts, dosage timing and other reminders.

BRIEF DESCRIPTION OF THE DRAWINGS

FIG. 1 shows a front view of an ejector device in an embodiment of the disclosure;

FIG. 2 shows a docking station of an embodiment of the disclosure;

FIG. 3 shows a system in an embodiment of the disclosure; and

DETAILED DESCRIPTION OF THE INVENTION

Figure 4:
FIGS. 4-8 show exemplary user interface depictions in accordance with embodiments of the disclosure.

A major concern in medical treatment of glaucoma, is the failure by subjects to regularly take their medication. Subjects either forget to take the medication or fail to take the correct dosage, e.g., to get the correct number of drops into the eye due to the difficulty of using a conventional eye dropper. In part, to address issues encountered with the use of conventional eye droppers, ejector devices, such as those described in U.S. Patent Publication No. 2011/0143152 filed concurrently herewith, entitled Drop-Generating Device, the contents of which are herein incorporated by reference in their entirety may be used in connection with the present disclosure.

As described in U.S. Patent Publication No. 2012/0143152, again herein incorporated by reference in its entirety, the ejector device may generally be device for delivering a fluid to an eye of a subject. For instance, the device may comprise: a housing; a reservoir disposed within the housing for receiving a volume of ophthalmic fluid; and an ejector mechanism configured to eject a stream of droplets to the eye of a subject upon activation of the device by a user. The ejected stream of droplets may have an average ejected droplet diameter greater than 15 microns and a low entrained airflow such that the ejected stream of droplets is deposit on the eye of the subject during use. In certain embodiments, the ejector device includes a piezo electric ejector mechanism comprising an ejector plate having a first surface coupled to a fluid delivery area of the reservoir and including a plurality of openings formed through its thickness, and a piezo electric actuator coupled to a second surface of the ejector plate, the piezo electric actuator operable to oscillate the ejector plate at a frequency and generate the ejected stream of droplets.

In another aspect, the disclosure provides a device for administering a fluid to the eye, such as an eye medication (e.g., anti-histamine) eye solution, eye lubricant or eye wetting agent, pupil dilator, fluorescein, anesthetic, suspended solid, etc., in a stream of droplets to the eye. However, the disclosure is not limited to use in connection with administration to the eye. For instance, other topical, inhaled, parenteral, oral, etc., delivery routes are envisioned as within the scope of the present disclosure. In one embodiment, the disclosure may be implemented using a device or applicator in the form of a thermal ejector, ultrasonic ejector, or piezo ejector generating ejected fluid droplets.

In one embodiment, an ejector device is provided with a memory for storing data such as subject-related information, e.g., dosing regimen information, etc. Any suitable memory or data storage media may be used, in certain embodiments, such memory may be in the form of a Flash memory drive with a universal serial bus (USB) port, which allows communication with a processing device, computer or user terminal. The Flash memory device (FMD) in one embodiment is pre-programmed to include its own user interface, which may be implemented as a graphical user interface (GUI). The FMD may include content data, e.g., subject information data, and applications. The GUI may include links for accessing at least some of the content data remotely. The GUI may also include Internet links, typically in the form of Web links. The FMD may be operable to launch a browser when an Internet link is clicked. The browser may be a browser that is installed on the processing device, computer or user terminal with which the FMD is in communication. Instead, a browser may be locally stored on the FMD or may be downloaded from a server. The FMD may be implemented to launch the browser automatically when the FMD is in communication with a processing device, computer, or user terminal, if such device, etc., is detected to have Internet access, or the browser may be launched manually by the user, e.g., by clicking an Internet link. In certain embodiments, the processing device, computer, user terminal, etc., may include a desktop computer, laptop, Personal Digital Assistant (PDA), smartphone, etc.

In certain embodiments, the ejector device may include an a controller or processor for controlling the dosing of a medicament (L e., dosing regimen). In order to ensure proper use by the subject, the controller may control dispensing of one or more medications to correspond to defined dosing times and dosing amounts and may monitor the amount of fluid dispensed during each dosing time to ensure delivery of the full dose. Such information may then be stored in the memory of the ejector device. The controller may also be programmed with dosage information (e.g., by a medical professional) and may be updated remotely to include new dosing information or new medication information, if needed.

More specifically, in one embodiment, with reference to FIG. 1, the present disclosure, in part, relates to an ejector device 100 having an alarm, which in this embodiment comprises an audible alarm, e.g., in the form of a speaker 110, a visual alarm, e.g., in the form of a LED 112 mounted on the device housing, a tactile alarm, e.g., a vibration mechanism (not shown).

The subject is notified when a dose needs to be taken, or a missed dose is detected. In an embodiment, a controller, processor or other programmable means (not shown) may be programmed with dosage and treatment regimen information to send a signal to the speaker 110 and/or LED 112 at the time a dose needs to be taken. In another embodiment, the device 100 alarm may be remotely initiated, e.g., by cell-phone, remote calendar, etc. Device 100 also may include a targeting mechanism 130 to aid in aligning dosing of the device. In certain aspects, targeting mechanism may be a low-intensity light beam, e.g., a low-intensity or filtered light emitting diode (LED) which emits a beam when, e.g., the ejector device is activated. In certain embodiments, the light beam may be configured to shine into the user's eye when the ejector device is correctly aligned with the eye. In other embodiments, ejector device 100 may include one or more illuminating devices, e.g., LEDs or other illuminating devices in addition to the targeting device 130, capable at illuminating at varying desired wavelengths. In certain instances, such illuminating devices may be useful in treatment or diagnosis of subjects alone or in connection with administration of agents (e.g., pupil-dilating agents, dyes, therapeutic agents, etc.). Alternatively, illuminating devices may be used in connection with image capture device 150 (below) to aid in obtaining quality image capture.

By way of example, the ejector device may include one more illuminating devices of varying wavelengths such as a red light, blue light, green light, white light, and/or IR light, which may be implemented by making use of LEDs. Monochromatic light sources may be used for monochromatic fundus imaging, preferably below 540 nm wavelength. This involves the imaging of the ocular fundus with the use of colored or monochromatic illumination to enhance the visual contrast of anatomical details of the fundus.

The device may also include an image capture device for obtaining images of the eye or structures of the eye (e.g., retina, pupil, cornea, etc.). By way of example, in the embodiment of FIG. 1, the image capturing device may comprise a camera in the form of a charge coupled device (CCD) 150, retinal scanner or other camera to capture images of the eye. In one embodiment, the images may include images showing the effect of pressure on the cornea, for purposes of diagnosing potential glaucoma, or may include images taken using different wavelength illumination to obtain information about the health of the eye, etc. The images may be stored in the memory in the device, and subsequently downloaded to the docking station and/or a remote memory or database, as discussed herein.

In some embodiments, the image capture device may be utilized to detect the presence of an eye and to ensure that the eye is open and/or that correct alignment of the eye is detected. The image capture device may provide information to the controller or processor, which, in one embodiment, provides a signal to initiate activation of the ejector device when opening of the eye and/or correct alignment of the eye, is detected. Alternatively, a reflective surface mounted on or incorporated within the ejector device, or an infra-red (IR) transmitter (e.g., IR LED) and photo detector may be mounted on the front surface of the ejector device (not shown). In certain aspects, the IR transmitter may transmit an infra-red beam or pulse, which is received by an IR photo detector when the ejector device is correctly aligned with the eye, and the IR beam or pulse is reflected off the eye and the beam or pulse is reflected to the IR photo detector.

In one embodiment, the ejector device described herein provides a user, e.g., a medical professional and/or subject, information regarding a subject's compliance with a particular dosage regimen. In one embodiment, the device includes a memory and controller, processor, etc., further includes software, programmable executable code, etc., to store information regarding dosing, e.g., the dates and times that the device is used and the volumes ejected. This information may be stored on a memory chip or other suitable memory storage media for subsequent retrieval. In certain implementations, the information may be retrieved via an input/output (I/O) port or wireless interface, such as a Universal Serial Bus (USB), an Infrared Data Association IrDA interface, a Bluetooth transceiver, etc.

It will be appreciated that the disclosure has been described with respect to different embodiments of the ejector device; however, the invention is not limited to the specific embodiments, but can be implemented in different ways without departing from the scope of the disclosure.

In another embodiment, the ejector device may communicate with a docking station. For example, with reference to FIG. 2, the ejector device may communicate with docking station 200. In certain embodiments, docking station 200 may generally include a memory (volatile, non-volatile, or combinations thereof), an I/O port or wireless interface for communicating with a public or private network, and a communication interface for communication with the ejector device. In certain embodiments, there may be a single communication interface for communicating with networks and the ejector device, or the docking station may include multiple communication interfaces. Docking station 200 may allow the data stored in memory of the ejector device to be downloaded or otherwise communicated to the docking station via, e.g., engagement of a docking port of the device with the communication interface of the docking station. Alternatively, input/output port or wireless interface of the ejector device may interface and/or communicate with the communication interface of the docking station. Such data may be downloaded or otherwise communicated on-demand (i.e., upon user docking), or at predetermined communication intervals (i.e., at predetermined times such that the ejector device attempts communication with the docking station, e.g., via a wireless communication network).

Docking station 200 may also include charging contacts (not shown) to engage with receiving contacts on the device to charge re-chargeable batteries in the device, if desired. In certain embodiments, the data may be stored in memory in the docking station 200. The docking station 200 may also be in communication, either wired or wirelessly, with a private or public network, e.g., via the I/O port or wireless interface of the docking station. In certain embodiments, data stored in memory of the device may be transferred or communicated, via the docking station and/or the I/O port of the device, and via a network to a remote server for storage in a remote memory or database.

In accordance with certain embodiments of the invention, the docking station may include a processor or controller, which in certain embodiments, may comprise software or computer executable code that enable functionality/diagnostics checks of the operation of the ejector device when the ejector device is in communication with the docking station, or at predetermined time intervals, etc.

In other embodiments (not shown), the docking station may include tactile, visual, and/or audible alarms. Such alarms may provide dosing reminders to a user, both on an automated treatment and a corrective treatment basis (e.g., based automated dosing regimen reminders and reminders if doses are missed). As explained herein, a medical professional may communicate with the ejector device through the communication interface of the docking station, or may communicate directly with the ejector device (e.g., to modify dosing regimen).

In another embodiment, a system including at least one ejector device and an optional docking station is provided. The systems of the present disclosure may also include the ability to communicate, e.g., via a communication network to a database or server, or user terminal. In one embodiment, a system for monitoring subject compliance with a dosing regimen is provided. Such systems can further be utilized to monitor and analyze treatment and, e.g., adjust dosing regimens accordingly, as discussed herein. Further, such systems may be used to diagnosis subjects based on data collected. The system generally comprising an ejector device configured for administering a stream of droplets to the eye of a subject in need thereof, wherein the ejector device comprises a memory for storing subject specific data and a communication interface for communicating the stored data. In some embodiments, the ejector device comprises an image capture device. In certain embodiments, the system further comprises a docking station configured to interface with the ejector device and to communicate with the ejector device.

In certain embodiments, the system comprises one or more databases or servers in communication with the ejector device(s). The databases or servers are configured to store data received from the ejector device, the docking station, or combinations thereof In some embodiments, the ejector device is in communication with the database or server via the docking station. In certain embodiments, the database or server may be a compliance database or an adherence database. The database or server may store one or more medical records for a user of the ejector device, and the record may include data collected by the ejector device. In certain embodiments, the database may be integrated with an Electronic Medical Record (EMR) system, as the term is understood by those of skill in the art.

By way of example, FIG. 3 illustrates a system 300 including an ejector device 301 interfaced (e.g., physically interfaced, in wired or wireless communication, etc.) with a docking station 302, which is networked (wired or wirelessly, including via a public or private network such as the Internet as depicted by the communication network cloud 304) for communicating data for storage in a memory of a database or a server 306. A user or medical professional, e.g., physician, or other expert located remotely at user terminal 310 can then access some or all of the data on the server or database 306. In certain embodiments, as understood by those in the art, the database or server 306 may be secured, e.g., by a user identification code or other security measure, to ensure that only authorized users have access to the data. Further, in certain embodiments, the database or server may be secured so as to only give access to certain portions of the data to certain users, etc. (e.g., based on subject privacy concerns). In certain aspects, the device 300, database or server 306, terminal 310, etc., may be configured to allow two-way communication, e.g., via communication network 304, such that a user may upload data to ejector device 300. By way of example, the data may include subject-specific information, such as compliance information, dosing regimen information, e.g., two drops twice a day of drug A in both eyes at defined times of the day, 1 drop in each eye of drug B, etc.

Although the example of FIG. 3 shows the database or server 306 as being separate (and at a separate location) from the ejector device 301, the base station 302, and the user terminal 310 (not shown) this is not necessarily the case. However, the database or server 306 may be co-located with the user terminal 310, or may be configured to interact with multiple devices similar to the ejector device 301, such that the database 306 may store information for multiple devices used by a particular user and/or information about multiple patients, each of whom use one or more devices such as the ejector device 301. Further, in some embodiments, database or server 306 may be distributed across multiple databases and servers, or the information may be distributed across database or server 306, and one or more of ejection device 301, base station 302, or user terminal 310.

In certain embodiments, a user may access, review and/or analyze data from an ejector device, database, server, etc., via a user interface such as a graphical user interface (GUI) on a computer in communication with the device, database, server, etc. Exemplary GUI embodiments are illustrated in FIGS. 4-8. FIG. 4 shows an overview page with various subject identifiers 400 (e.g., names and dates of birth). Column 402 defines a right and left eye treatment for each subject. Columns 404 provide individual columns for the various treatment weeks, each eye for each subject being, e.g., coded to indicated full compliance by the subject with dosage requirements (green), partial compliance (orange) or no compliance (red). In another embodiment (not shown) coding may be used to indicate different drug types.

Figure 5:
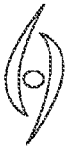
Figure 6:
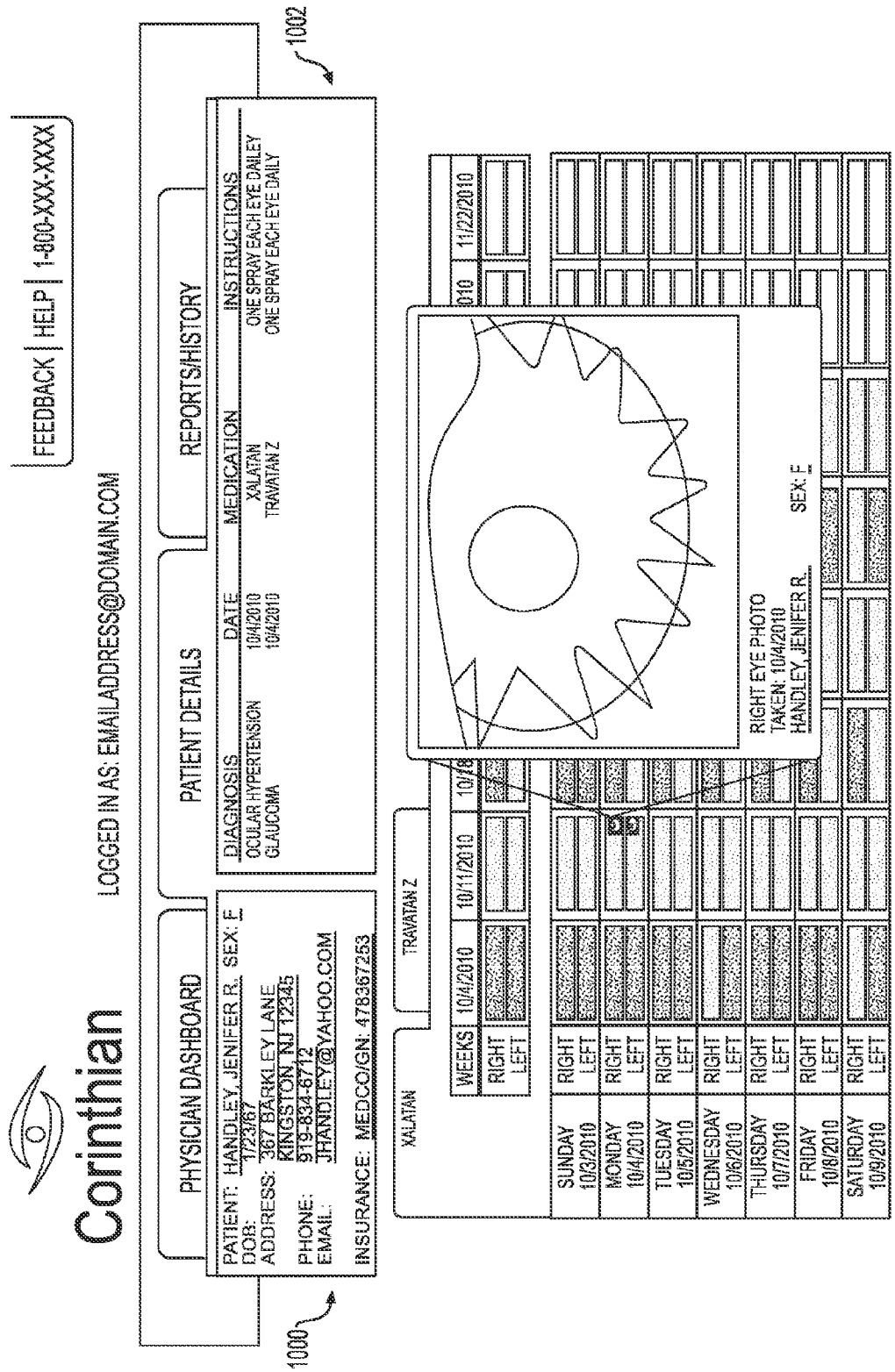

FIG. 5 shows an individual subject record. The various columns correspond to information by week, and the rows correspond to each day. The upper portion provides subject details 500 and treatment regimen details 502. As shown in FIG. 6, clicking on any of the cells in the subject detail array allows additional information to be viewed, insofar as there is additional information, such as images captured of the eye, date of the image and subject details, etc., thereby allowing a visual record over time. This allows a medical professional to remotely monitor not only subject compliance with dosing regimen, but also to remotely monitor visual diagnostic information and interact with the subject as needed.

Figure 7:
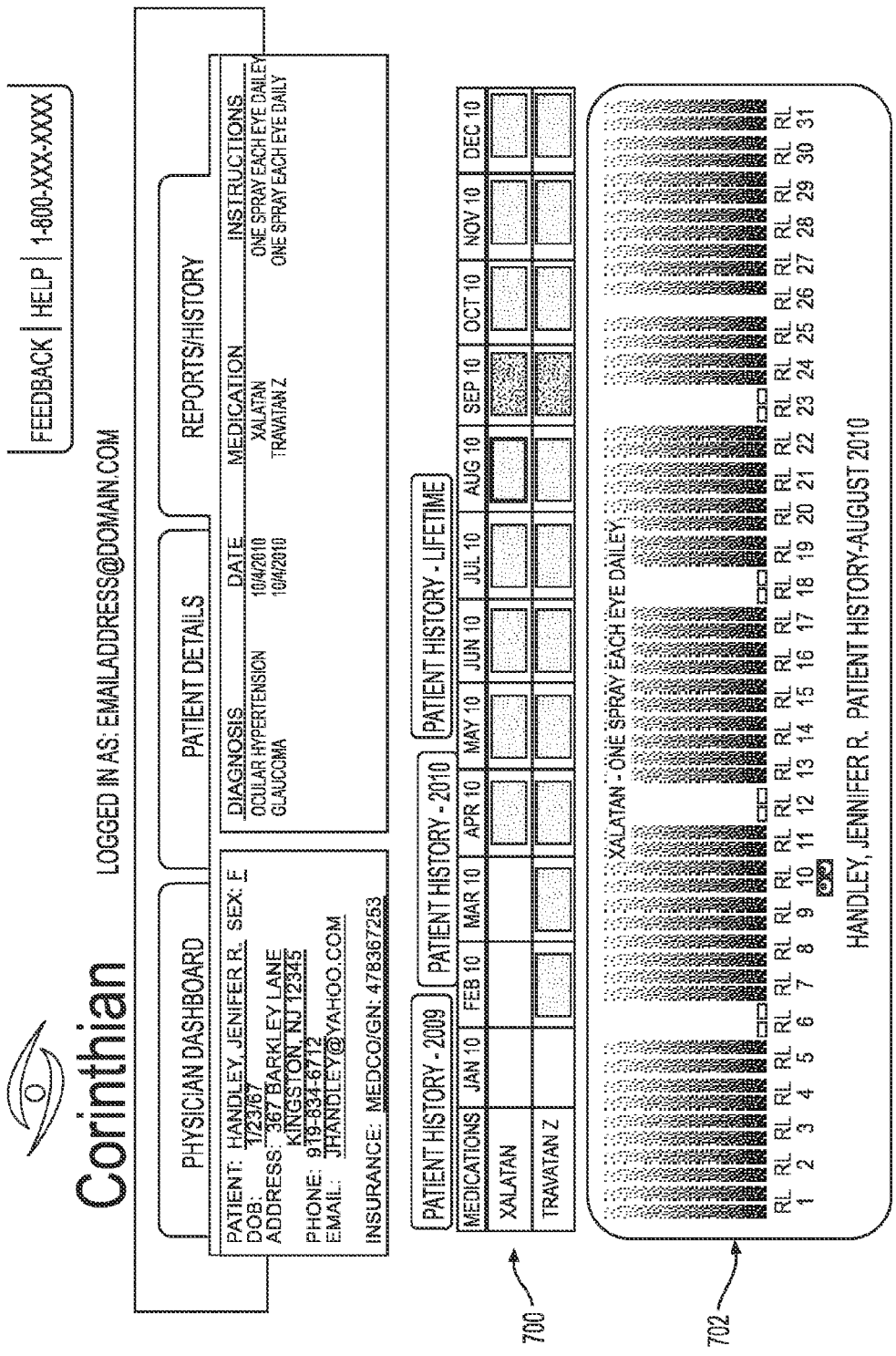
Figure 8:
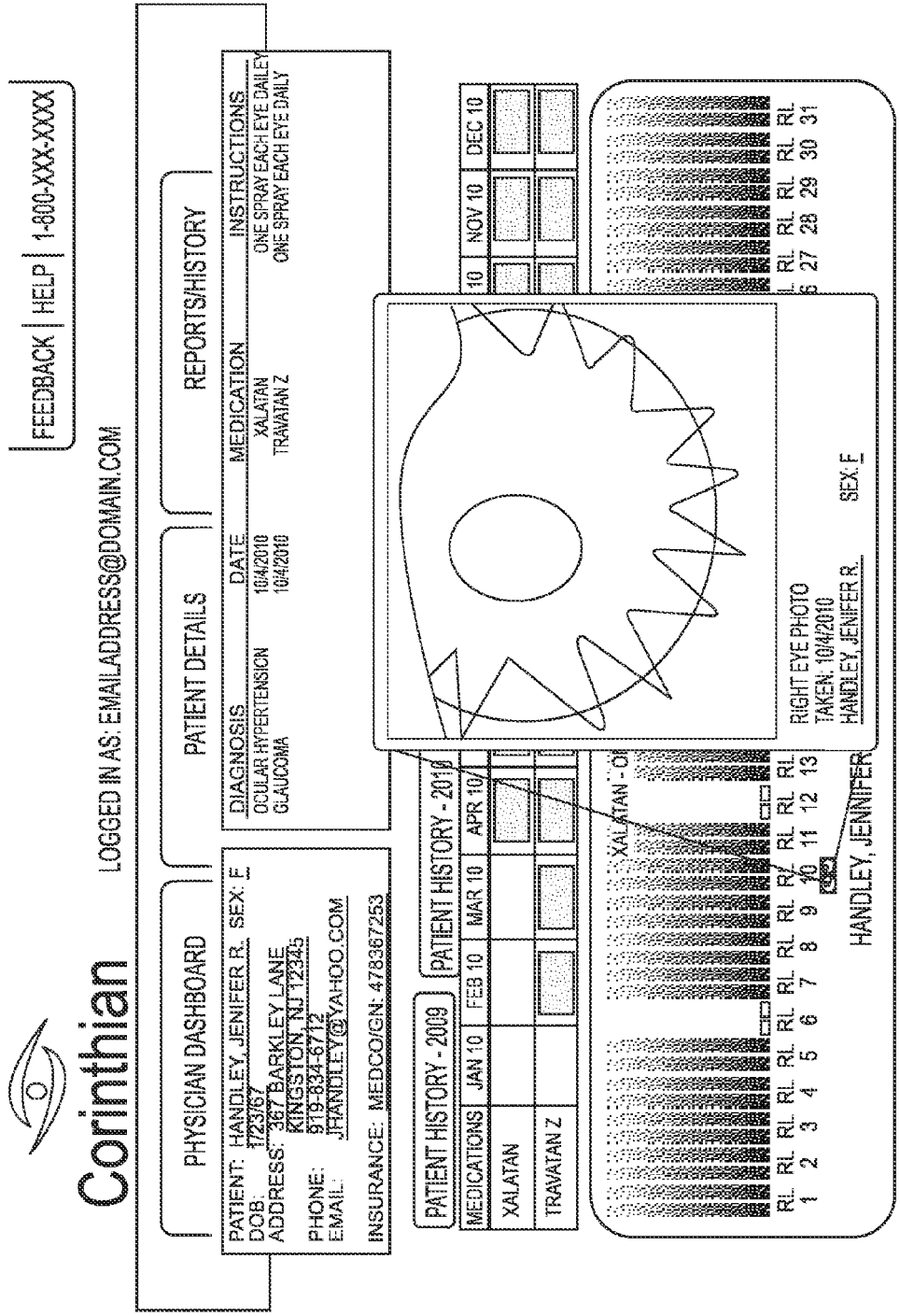

FIG. 7 illustrates yet another embodiment including subject compliance detail information. FIG. 7 shows compliance data detail, e.g., for each medicament to be administered per a dosing regimen in section 700, and a graphical display 702 showing level of compliance for each eye and a selected medicament. As shown in FIG. 8, clicking on any of the cells in the subject detail array allows additional information to be viewed, insofar as there is additional information, such as images captured of the eye, date of the image and subject details, etc., thereby allowing a visual record over time. Again, this allows a medical professional to remotely monitor not only subject compliance with dosing regimen, but also to remotely monitor visual diagnostic information and interact with the subject as needed.

In certain embodiments, the systems and ejector devices described herein allow for the remote monitoring of one or more subjects, and may allow a medical professional to remotely diagnosis, treat and adjust treatment as needed. By way of example, the systems and ejector devices may allow for the capturing, storage, and communication of data related to dosing regimen compliance information, image information, etc., which information may be reviewed and analyzed. If desired, the information may be compared to earlier information related to the same subject, information from multiple subjects (i.e., information from multiple subjects may be stored in a central database and compared based on demographics information about the users, dosage and type of medicament, etc.).

In yet another embodiment, methods are provided which generally include: (1) administering a stream of droplets to the eye of a subject in need thereof using an ejector device, such as those described herein; and (2) storing data in a memory of the device, the data relating to, e.g., dosing regimen information, image information, etc. In certain embodiments, the method may further including (3) communicating the stored data from the ejector device, e.g., to a docking station, database or server, and/or user terminal. The communicated data may then be stored in memory in the docking station, the database or server, or in a memory on the user terminal. In yet other embodiments, the data communicated from the device (e.g., from the docking station, database or server, or via the user terminal) may be reviewed and analyzed. Based on such review and analysis, in one embodiment, the method may include adjusting dosages and medicaments as needed. In one example, if desired results are not observed in the data, the dosage regimen may be increased (dosage amounts, number of dosages, etc.). Alternatively, if results indicate such, the dosage regimen may be decreased. In yet another embodiment, the ejector device may include two or more medicaments, wherein a first medicament is used and monitored for a first period of time and if the desired results are not achieved, administration is changing to a second or third medicament.

In another embodiment, the ejector device may include an image capturing device, and the method may include communicating image information (e.g., ocular image information). The method may include reviewing and analyzing the image information to diagnose the subject, e.g., by comparing image information to previous images obtained from the same subject or to images obtained from other subjects. In some embodiments, image information may be obtained independently of administration of a stream of droplets, prior to such administration, concurrently with such administration, subsequent to such administration, or a combination thereof.

In one embodiment, a method for monitoring ophthalmic subjects is provided. The method generally includes administering a stream of droplets to the eye of a subject in need thereof using an ejector device described herein (e.g., a device including a memory for storing subject-specific data and a communication interface for communicating said stored data); and storing said data in the memory of the device. The method can further include analyzing the communicated data from the ejector device and adjusting administration of the stream of droplets to the eye of the subject as needed, based on said analysis.

In other embodiments, the method includes receiving subject-specific data from an ejector device, the ejector device configured for administering a stream of droplets to the eye of a subject in need thereof; storing the data in at least one database; analyzing the stored data; and adjusting administration of the stream of droplets to the eye of the subject as needed, based on said analysis.

In yet other embodiments, the ejector device may further include an image capturing device for capturing images of the eye of the subject. The method may further include capturing images of the subject's eye; and storing the images in the memory of the device.

In one embodiment, the subject is being treated for glaucoma, and the stream of droplets administered to the eye comprises a medicament for the treatment of glaucoma. In certain embodiments, the subject-specific data includes dosing regimen information related to the treatment of glaucoma, information related to the subject's compliance with the dosing regimen, etc.

In yet another embodiment, a method for diagnosis of ophthalmic subjects is provided. The method generally includes: capturing images of a subject's eye using an ejector device; storing the images in the memory of the device; and analyzing the images to thereby diagnose the subject based, at least in part, on analysis of said images.

In another embodiment, methods for the diagnosis for glaucoma are provided, which typically include the exertion of pressure on the cornea, e.g., Goldmann applanation tonometry, and which involves the application of Fluress® (comprising a fluorescent agent, an anesthetic, a preservative, and a wetting agent and stabilizing agent), followed by the applanation using a 3.06 mm$^2$ device. For intraocular pressures of 20 mmHg or less, the accuracy of the measurement should be within +0.5 and −0.5 mmHg The present disclosure provides a method for diagnosis of glaucoma, generally comprising applying pressure to avoid the use of an applanation device. By ejecting a selectable number of droplets of liquid, e.g., saline solution onto the eyeball from a defined distance, the pressure exerted on the cornea and intraocular pressure can be determined based on the deformation, which can be captured by the image capture device. In one embodiment, a reservoir includes a saline compartment, which is manually selectable by means of a selector switch mounted on the device, or the saline compartment is selected by having the physician upload medication type and dose information that selects a certain number of droplets of saline solution to define a certain pressure. Feedback information captured by the image capture device may be uploaded to the database or server, to allow the doctor to diagnose the condition and either adjust the pressure of a second ejection cycle or schedule a follow-up appointment for the subject.

In certain embodiments, the systems and methods of the disclosure may be used to monitor the treatment of chronic problems such as glaucoma. Stored data may be reviewed and analyzed, e.g., to evaluate patient compliance, to evaluate efficacy of dosing regimen, to determine necessary changes to dosing regimen, and to implement changes as needed.

The systems and methods of the present disclosure may also be used for situational applications, such as the delivery of medication after cataract or other ophthalmic surgery to facilitate self-administration of prescribed medications at defined times and defined dosages. Other embodiments include, but are not limited to: conjunctivitis treatments; allergy treatments; saline application for those who wear contact lenses; sore, irritated, red-eye treatments; application of dilation medications; decongestants that shrink or constrict blood vessels and cause the eye to whiten; corticosteroids such as Prednisolone®, Dexamethasone®, Hydrocortisone®, Fluoromethalone®, Medrysone®, Rimexolone®, etc.

In the case of medicaments where the exact or low dosage is of importance, the systems and methods of the disclosure may be of particular use. For instance, some of the medications that can be dispensed using the device of the invention include, but are not limited to: glaucoma medications such as ocular hypotensive agents for glaucoma, including but not limited to the prostaglandin analogues, such as Xalatan® (latanoprost) by Pfizer, Lumigan® (bimatroprost,) by Allergan, Travatan® (travoprost) by Alcon may be applied; alpha agonists such as Alphagan® P (brimonidine) by Allergan, and Combigan® (brimonidine/timolol) by Allergan, and beta blockers such as Timolol®; carbonic anhydrase inhibitors such as Trusopt® (dorzolamide) by Merck, Cosopt® (dorzolamide/timolol) by Merck, and Azopt® (brinzolamide) by Alcon; antibiotics such as "4$^{th}$ Generation" Fluoroquinolones for perioperative infection prophylaxis); Zymar® (gatifloxacin) by Allergan; Vigamox® (moxifloxacin) by Alcon; anti-inflammatory such as steroids like Prednisolone® acetate 1%-generic, Pred forte® by Allergan, Omnipred® by Alcon, and Difluprednate (Durezol®) by Alcon; non-steroidal such as Acuvail® (ketorolac) by Allergan, Xibrom® (bromfenac) by Ista; Nevanac® (nepafenac) by Alcon, and Ketorolac®; combination antibiotic/steroid preparations frequently used for post operative subjects, including Tobradex® (tobramycin/dexametasone solution, Alcon); etc.

As discussed herein, medicaments are generally discussed in the context of ophthalmic medication including a therapeutically active agent. However, medicaments are not so limited and include all ophthalmic liquids, such as an eye medication (e.g., anti-histamine) eye solution, eye lubricant or eye wetting agent, pupil dilator, fluorescein, anesthetic, etc.

In another embodiment, providers can get onto the system and through a user interface, set parameters of a database so that the device will read to adjust dosage amounts, dosage timing and other reminders. Additionally, with patient-identifying information removed, such as for example in accordance with HIPAA privacy policies, this database becomes a significant asset for example to pharmaceutical companies for data mining and insurance companies for underwriting. Once patient-identifying data is scrubbed, a host of reports can be generated for interested parties. Indeed, the capabilities of this database, in combination with the device, promise a new standard of care in the industry, providing a comprehensive solution to improve overall compliance/adherence, minimize office visits, reduce probability of blindness due to glaucoma and improve quality of life.

The present disclosure has been disclosed with reference to specific embodiments. It will, however, be appreciated that the invention is not so limited.

What is claimed is:

1. A system for treating ophthalmic subjects, comprising:
    at least one piezo electric ejector device configured for administering an ejected stream of droplets to the eye of a subject in need thereof upon activation of said ejector device by a user;
    said at least one ejector device comprising: a housing; a reservoir disposed within the housing for receiving a volume of ophthalmic fluid; an ejector mechanism comprising an ejector plate having a first surface coupled to a fluid delivery area of the reservoir, the ejector plate including a plurality of openings formed through its thickness; and a piezo electric actuator coupled to a second surface of the ejector plate, the actuator being operable to oscillate the ejector plate at a frequency to thereby generate the ejected stream of droplets upon actuation;

a memory for storing subject-specific data;

a communication interface for communicating said stored subject-specific data;

an image capture device for obtaining images of the eye or structures of the eye of said subject sufficient to obtain information about the diagnosis or health of the eye, the subject-specific data including image information captured by said image capture device, and at least one database or server in communication with said at least one ejector device via said communication interface.

2. A system of claim 1, further comprising at least one docking station comprising a communication interface for communicating with said at least one ejector device.

3. A system of claim 2, wherein said communication interface of said at least one ejector device and said communication interface of said at least one docking station are each individually selected from a wired or wireless communication interface.

4. A system of claim 2, wherein said at least one ejector device comprises at least one I/O port configured to interface with said communication interface of said at least one docking station.

5. A system of claim 2, wherein said at least one ejector device is in communication, with said at least one database or server via said at least one docking station.

6. A system of claim 1 wherein the image capture device is a charge coupled device (CCD) configured capture images of the eye or structures of the eye at different wavelength illuminations.

7. A system of claim 1, further comprising a user terminal.

8. A system of claim 7, wherein said user terminal is selected from the group consisting of a computer, a smartphone, and a PDA.

9. A system of claim 7, wherein said system is configured for two-way communication between said at least one ejector device and said user terminal via a communication network.

10. A method for monitoring the treatment of ophthalmic subjects, the method comprising:

administering an ejected stream of droplets to the eye of a subject in need thereof using a piezo electric ejector device, said ejector device comprising: a housing: a reservoir disposed within the housing for receiving a volume of ophthalmic fluid; an ejector mechanism comprising an ejector plate having a first surface coupled to a fluid delivery area of the reservoir, the ejector plate including a plurality of openings formed through its thickness; and a piezo electric actuator coupled to a second surface of the ejector plate, the actuator being operable to oscillate the ejector plate at a frequency to thereby generate the ejected stream of droplets upon actuation; a memory for storing subject-specific data; an image capture device for obtaining images of the eye or structures of the eye of said subject sufficient to obtain information about the diagnosis or health of the eye the subject-specific data including image information captured by said image capture device; and a communication interface for communicating said stored subject-specific data;

capturing images of the eye or structures of the eye of said subject sufficient to obtain information about the diagnosis or health of the eye prior to, concurrently with, subsequent to, or a combination thereof, said administration of the ejected stream of droplets to the eye of said subject;

storing said subject-specific data including image information in the memory of said piezo electric ejector device;

communicating said stored subject-specific data from said piezo electric ejector device to a docking station, database or server, and/or user terminal; and analyzing the communicated subject-specific data to thereby monitor the treatment of said ophthalmic subject.

11. A method of claim 10, wherein said analysis comprises comparing said images of the eye or structures of the eye of said subject to previous images captured of the eye or structures of the eye of said subject.

12. A method of claim 10, further comprising adjusting administration of said ejected stream of droplets to the eye of said subject based on said analysis.

13. A method of claim 10, wherein said subject is being treated for glaucoma, and said stream of droplets administered to the eye comprises a medicament for the treatment of glaucoma.

14. A method of claim 13, wherein said subject-specific data includes dosing regimen information related to the treatment of glaucoma.

15. A method of claim 14, wherein said subject-specific data includes information related to said subject's compliance with the dosing regimen.

16. A method for monitoring the treatment of ophthalmic subjects, the method comprising:

receiving subject-specific data at, at least one database or server via a communication network via a communication interface of a piezo electric ejector device used to administer an ejected stream of droplets to an eye of a subject need thereof and to capture images of the eye or structures of the eye of said subject sufficient to obtain information about the diagnosis or health of the eye prior to, concurrently with, subsequent to, or a combination thereof, said administering of the ejected stream of droplets to the eye of said subject, the subject-specific data comprising said images of the eye or structures of the eye of the subject sufficient to obtain information about the diagnosis or health of the eye;

storing said subject-specific data in the at least one database or server; and analyzing the stored subject-specific data to thereby monitor the treatment of said ophthalmic subject.

17. A method of claim 16, further comprising adjusting administration of said ejected stream of droplets to the eye of said subject based on said analysis.

18. A method of claim 16, wherein said subject is being treated for glaucoma, and said stream of droplets administered to the eye comprises a medicament for the treatment of glaucoma.

19. A method of claim 18, wherein said subject-specific data includes dosing regimen information related to the treatment of glaucoma.

20. A method of claim 19, wherein said subject-specific data includes information related to said subject's compliance with said dosing regimen.

21. A method of claim 16, wherein said analysis comprises comparing said images of the eye or structures of the eye of said subject to previous images captured of the eye or structures of the eye of said subject.

* * * * *